(12) United States Patent
Finkman et al.

(10) Patent No.: US 9,713,502 B2
(45) Date of Patent: Jul. 25, 2017

(54) NARROW BAND IMAGING WITH SURGICAL LOUPES

(71) Applicant: GYRUS ACMI, INC., Southborough, MA (US)

(72) Inventors: Shai Finkman, Haifa (IL); Shani Rosen, Tel Aviv (IL); Philip Alper, Misgav (IL)

(73) Assignee: GYRUS ACMI, INC., Southborough, MA (US)

( * ) Notice: Subject to any disclaimer, the term of this patent is extended or adjusted under 35 U.S.C. 154(b) by 319 days.

(21) Appl. No.: 14/201,863

(22) Filed: Mar. 9, 2014

(65) Prior Publication Data

US 2015/0253589 A1    Sep. 10, 2015

(51) Int. Cl.

| | |
|---|---|
| *G02F 1/01* | (2006.01) |
| *A61B 19/00* | (2006.01) |
| *G02C 7/08* | (2006.01) |
| *G02C 7/10* | (2006.01) |
| *G02B 25/00* | (2006.01) |
| *A61B 90/30* | (2016.01) |
| *A61B 90/50* | (2016.01) |

(52) U.S. Cl.
CPC .............. *A61B 19/26* (2013.01); *A61B 90/30* (2016.02); *A61B 90/50* (2016.02); *G02B 25/008* (2013.01); *G02C 7/088* (2013.01); *G02C 7/101* (2013.01); *A61B 2090/304* (2016.02); *A61B 2090/502* (2016.02); *Y10T 29/49016* (2015.01); *Y10T 29/49826* (2015.01)

(58) Field of Classification Search
CPC .......... G02B 25/008; G02B 1/02; G02B 3/00; G02B 25/004; G02B 5/208; G02B 21/14; G02B 21/24; G02B 21/22; A61B 19/00; A61B 19/5202; A61B 19/26; A61B 2019/5204; A61B 3/113; A61B 5/0059; A61B 90/50; A61B 90/30; A61B 2090/304; A61B 2090/502; G02C 7/10; G02C 11/00; G02C 5/00; G02C 7/12; G02C 7/02; G02C 7/08; G02C 7/101; G02C 7/088; G02F 1/01; G02F 1/015; G02F 1/1521; G02F 1/1523; Y10T 29/49016; Y10T 29/49826
USPC .......... 351/209, 158, 41, 49, 159.01, 159.27, 351/159.39; 359/481, 359, 385, 368, 371, 359/372, 240, 245, 256, 272, 275, 722; 600/473, 476
See application file for complete search history.

(56) References Cited

U.S. PATENT DOCUMENTS

| | | | |
|---|---|---|---|
| 4,991,941 A * | 2/1991 | Kalmanash | ....... G02F 1/133533 349/117 |
| 5,114,218 A | 5/1992 | Black et al. | |
| 5,184,156 A | 2/1993 | Black et al. | |
| 5,708,490 A | 1/1998 | Wieczorek | |

(Continued)

*Primary Examiner* — Jie Lei
(74) *Attorney, Agent, or Firm* — D. Kligler I.P. Services Ltd.

(57) ABSTRACT

Apparatus, including a housing that is configured to be mounted in proximity to a human eye. The apparatus further includes optics that is retained by the housing and that is configured to focus optical radiation from a scene to an image viewable by the human eye. The apparatus also includes a tunable wavelength filter that is retained by the housing and that is configured to sequentially filter the optical radiation from the scene by a first wavelength and by a second wavelength different from the first wavelength.

18 Claims, 8 Drawing Sheets

(56) References Cited

U.S. PATENT DOCUMENTS

| | | | |
|---|---|---|---|
| 6,459,919 B1 | 10/2002 | Lys et al. | |
| 6,501,443 B1* | 12/2002 | McMahon | G02C 7/101 |
| | | | 345/52 |
| 6,827,577 B1 | 12/2004 | Fulbrook | |
| 7,992,573 B2 | 8/2011 | Wilson et al. | |
| 8,272,343 B1 | 9/2012 | Weaver et al. | |
| 2004/0109231 A1* | 6/2004 | Haisch | A61B 5/0066 |
| | | | 359/385 |
| 2006/0004292 A1 | 1/2006 | Beylin | |
| 2009/0227847 A1 | 9/2009 | Tepper et al. | |
| 2010/0305436 A1* | 12/2010 | Chen | A61B 5/742 |
| | | | 600/431 |

* cited by examiner

NARROW BAND IMAGING WITH SURGICAL LOUPES

FIELD OF THE INVENTION

The present invention relates generally to imaging, and specifically to imaging using a surgical loupe.

BACKGROUND OF THE INVENTION

There are a number of references which describe particular methods for imaging and viewing of an object. Some of these references are briefly described below.

U.S. Pat. No. 8,272,343 to Weaver et al., whose disclosure is incorporated herein by reference, describes an apparatus and method for developing latent fingerprints. The apparatus has a heat source and a sublimation system that is in communication with the heat source. A light source excites a sublimation dye causing photoluminescent emissions which are viewed through filter goggles.

U.S. Pat. No. 7,992,573 to Wilson, et al., whose disclosure is incorporated herein by reference, describes a system having an optically-guided catheter. The system includes an external detection device that detects transdermally projected light, emitted by a light-emitting point from within the patient, and is claimed to indicate precise placement of the catheter within the patient.

U.S. Pat. No. 6,827,577 to Fulbrook, whose disclosure is incorporated herein by reference, describes a night vision goggle training apparatus that simulates the size, feel and handling of actual night vision goggles. A narrow bandwidth green filter is positioned over the viewing port, to simulate nighttime viewing conditions.

U.S. Pat. No. 5,708,490 to Wieczorek, whose disclosure is incorporated herein by reference, describes goggles for use with laser projection systems, and that allow passage of a narrow band of red wavelengths that surround the wavelength at which the laser is projecting. The goggles block adjacent wavelengths, and the disclosure claims that the laser image is in contrast, and is easily seen by a wearer. At the same time, the goggles pass at least a portion of the blue and green wavelengths.

U.S. Pat. No. 5,114,218 to Black, et al., whose disclosure is incorporated herein by reference, describes liquid crystal sunglasses with selectively color adjustable lenses. Each lens consists of a color mosaic mask and voltage-controlled active matrices. When a wearer of the sunglasses wants to change the color of the lenses he/she moves a switch to select a color, whereupon a battery cell is electrically connected with respective pixel sets of the active matrices.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides apparatus, including:

a housing, configured to be mounted in proximity to a human eye;

optics, retained by the housing and configured to focus optical radiation from a scene to an image viewable by the human eye; and a tunable wavelength filter, retained by the housing and configured to sequentially filter the optical radiation from the scene by a first wavelength and by a second wavelength different from the first wavelength.

In a disclosed embodiment the apparatus includes a neutral density filter retained by the housing and configured to apply a first transmission level to the optical radiation filtered by the first wavelength and to apply a second transmission level to the optical radiation filtered by the second wavelength.

Typically the apparatus includes a processor configured to measure a contrast of the image and to select the first wavelength and the second wavelength so as to maximize the contrast.

In a further disclosed embodiment the first wavelength includes a first narrow pass-band set of wavelengths and the second wavelength includes a second narrow pass-band set of wavelengths.

In a yet further disclosed embodiment the apparatus includes a reference sensor configured to acquire a reference image of the scene, and to determine the first wavelength and the second wavelength in response to a characteristic of the reference image. The characteristic may be a contrast metric measuring contrast within the scene, and the first wavelength and the second wavelength may be determined in response to the contrast metric being a maximum. Alternatively or additionally, the contrast metric may include a sub-element metric measuring contrast of a sub-element within the scene, and the first wavelength and the second wavelength may be determined in response to the sub-element metric being a maximum.

Typically, the apparatus includes a processor configured to apply a first transmission level to the optical radiation filtered by the first wavelength and to apply a second transmission level to the optical radiation filtered by the second wavelength. The processor may activate the tunable wavelength filter to sequentially filter at the first wavelength and the second wavelength according to a duty cycle determined in response to the first transmission level and the second transmission level.

In an alternative embodiment the scene is illuminated by broadband optical radiation, and the first wavelength includes a first pass-band wavelength narrower than the broadband optical radiation and the second wavelength includes a second pass-band wavelength narrower than the broadband optical radiation.

In a further alternative embodiment the tunable wavelength filter includes an electronically selectable filter wherein the first wavelength and the second wavelength are electronically selectable.

In a yet further alternative embodiment the tunable wavelength filter includes a mechanically selectable filter wherein the first wavelength and the second wavelength are mechanically selectable.

There is further provided, according to an embodiment of the present invention, a method, including:

mounting a housing in proximity to a human eye;

retaining optics, configured to focus optical radiation from a scene to an image viewable by the human eye, within the housing; and retaining a tunable wavelength filter, configured to sequentially filter the optical radiation from the scene by a first wavelength and by a second wavelength different from the first wavelength, by the housing.

The present invention will be more fully understood from the following detailed description of the embodiments thereof, taken together with the drawings in which:

DETAILED DESCRIPTION OF EMBODIMENTS

Overview

An embodiment of the present invention provides a medical professional, such as a surgeon, the opportunity of increasing the contrast of a scene being viewed during open surgery. During the surgery the scene is normally illuminated by broadband optical radiation, i.e., white light. Typically, surgical loupes are attached to spectacles being worn by the professional, the loupes focusing optical radiation from the scene to an image viewable by the professional.

In addition to having optics which typically provide the professional with a magnified view of the scene, each loupe comprises a tunable wavelength filter. The filter may be tuned to pass selected narrow pass-bands of the optical radiation returning from the scene being viewed. The filter is configured to sequentially filter different narrow pass-bands, so that the image viewed by the professional comprises a combination of the different filtered images, the images effectively being combined within the eyes of the professional, by virtue of the persistence of vision effect.

Each loupe typically also comprises means to set a transmission level for each of the different narrow pass-bands. The means may comprise a neutral density filter, having a variable neutral density which may be set. Alternatively, an effective transmission level for the narrow pass-bands may be accomplished by setting a duty cycle for the filters, the duty cycle providing a time of activation for each of the different narrow pass-bands.

Settings for the narrow pass-bands and their respective transmission levels may be determined using a reference sensor, which may be attached to the spectacles. The reference sensor comprises an array which acquires images, of the scene being viewed, at the different pass-bands and transmission levels. The different images may then be analyzed to determine the combination of pass-bands and transmission levels at which the loupes should be set to maximize the contrast of the scene being viewed. Alternatively, the combination may be determined, prior to the professional using the loupes, by acquiring images at different pass-bands and transmission levels, of a scene that is similar to the viewed scene.

In some embodiments the tunable wavelength filter comprises an electronically tunable filter, wherein a narrow pass-band of the filter is selectable electronically. In alternative embodiments, the tunable wavelength filter comprises a mechanically tunable filter, wherein one of a plurality of narrow pass-band filters is selectable mechanically. Similarly, the neutral density filter may be configured so that its density is selectable electronically or, alternatively, so that its density is selectable mechanically.

Embodiments of the present invention thus provide, for an open surgery situation, a medical professional with a method for increasing the contrast of the scene of the open surgery. Such a method has to date only been available for a closed surgery situation, that is typically viewed using an endoscope.

Detailed Description

Figure 1:
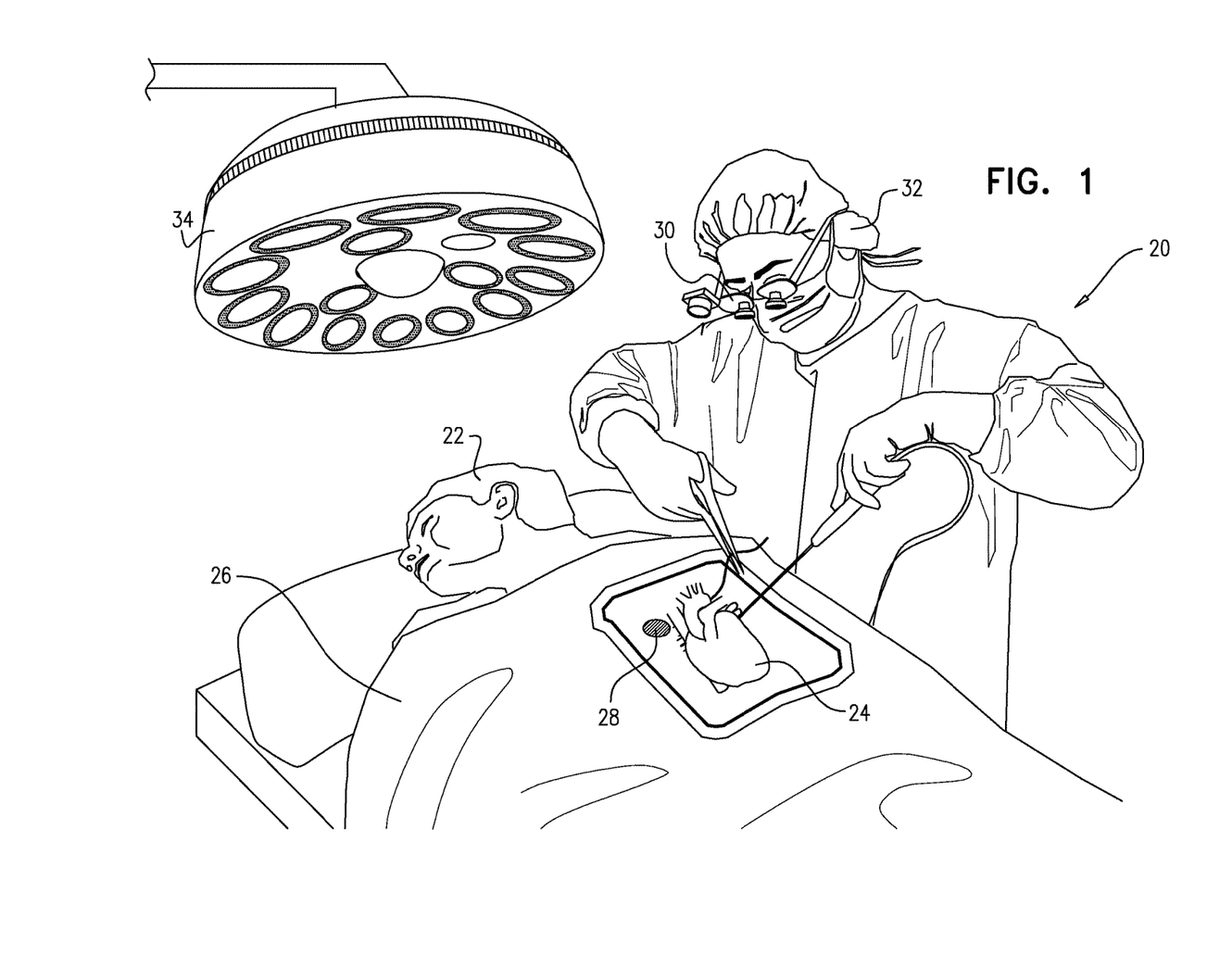
FIG. 1 is a schematic illustration of a surgical viewing system, according to an embodiment of the present invention.

Reference is now made to FIG. 1, which is a schematic illustration of a surgical viewing system 20, according to an embodiment of the present invention. As is explained further below, system 20 improves the contrast of a scene being viewed by an operator of the system. The system may typically be used in a medical procedure involving open surgery, such as a procedure involving open chest surgery, in order to view part or all of the entities exposed during the surgery, and to improve the contrast of a sub-set of these entities. By way of example, in the present description a region 24 within a chest 26 of a patient 22 is assumed to have been exposed, and a section 28 of the region is viewed by a medical professional 32 operating the system. In the following description, section is assumed to be illuminated by an overhead lamp 34 that illuminates region 24 with broadband optical radiation appearing substantially as white light. While the description herein is directed to enhancing contrast in an exposed region within chest 26, it will be understood that system 20 may be used to enhance contrast in substantially any exposed region within a human body, such as the abdomen, or an extremity, or an unexposed region of the body or of another entity.

System 20 comprises a pair of spectacles 30, also herein termed spectacles 30, which are worn by the professional in order for the professional to view section 28. As is explained below, by wearing and using spectacles 30, the visibility of selected elements within the section may be enhanced, by improving their contrast, and the professional may choose which elements, or types of elements, have their visibility enhanced.

Figure 2:
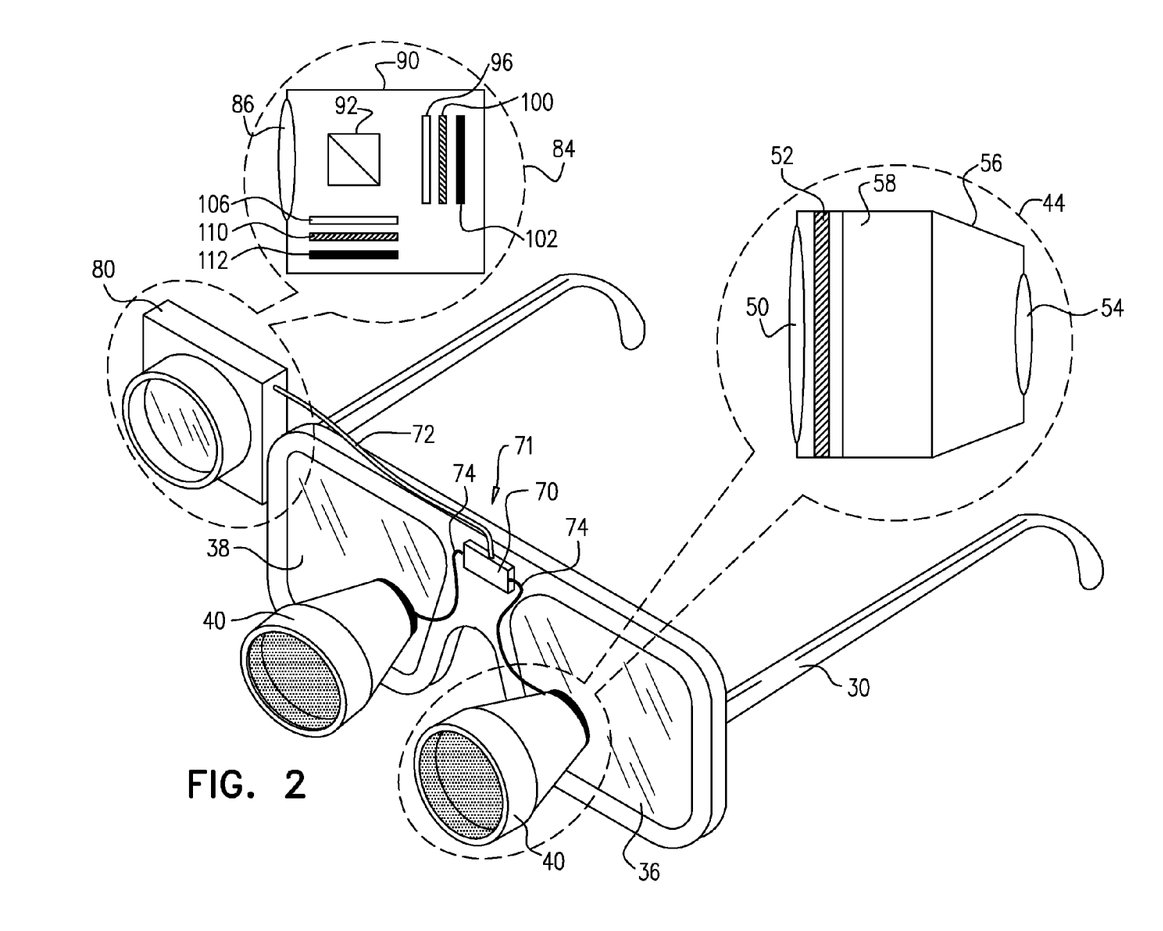
FIG. 2 is a schematic drawing of a pair of spectacles, according to an embodiment of the present invention.

FIG. 2 is a schematic drawing of spectacles 30, according to an embodiment of the present invention. Spectacles 30 comprise a spectacle frame, within which are mounted lenses 36 and 38 adapted for correction of the sight of professional 32. In the case where the professional does not require corrective lenses, lenses 36 and/or 38 may be plane glass or plastic.

Mounted on lenses 36 and 38 are two loupes 40, which typically allow the professional to view section 28 of region 24 as a magnified section. While loupes 40 have generally the same structure and function, each loupe and its mounting on lenses 36 and 38 may be customized for an individual professional, taking into account the professional's corrected vision, inter-pupillary distance and desired focal distance. An inset 44 is a schematic diagram illustrating the structure of loupe 40.

Each loupe 40 comprises an objective lens 50 and an eyepiece lens 54 which are mounted within a loupe housing 56. The light entering a given loupe 40 from section 28 is filtered by a tunable filter 58, which is attached to loupe housing 56. Filter 58 is typically able to be electronically tuned to filter light within a selectable narrow band of wavelengths, so that the filter acts as a tunable narrow band-pass filter. A suitable type of electronically tunable filter for filter 58 is a liquid crystal tunable filter (LCTF) or an acousto-optical tunable filter (AOTF), such as the "VariSpec" LCTF produced by PerkinElmer Inc, Waltham, Mass.

Each loupe 40 also comprises a variable neutral density filter 52, which is typically electronically tunable, and which may be constructed from a polarizer and a liquid crystal. Depending on the potential applied to filter 52, the transmission of the light through the filter may be varied from approximately 100% to approximately 0%.

System 20 is operated by a system controller 70, which typically comprises a central processor unit (CPU), and which also comprises a memory 71. Controller 70 may typically be implemented as an application specific integrated circuit (ASIC). Controller 70 acts as a data processor, and may be mounted on spectacles 30; for example, and as illustrated in FIG. 2, controller 70 may be mounted on the bridge of the spectacles. Controller 70 is connected electrically by connections 74 to filters 52 and 58 of loupes 40. The controller is thus able to select a pass-band for each of the loupes, and a transmission level for the radiation transmitted in the pass-band, by transferring appropriate control signal levels to filters 52 and 58.

A reference sensor 80, operated by controller 70 via a connection 72, is mounted on spectacles 30 and is configured to acquire an image of section 28, i.e., of the region being viewed by loupes 40. An inset 84 is a schematic diagram illustrating the structure of sensor 80. A sensor objective lens 86 of the sensor, mounted in a sensor housing 90, transfers radiation from section 28 to a beamsplitter 92, typically a 50/50 beamsplitter. From the beamsplitter, the radiation transfers in two paths. In a first path, the radiation is focused via a tunable band-pass filter 96 and a variable neutral density filter 100 onto a sensor array 102. In a second path the radiation is focused via a tunable band-pass filter 106 and a variable neutral density filter 110 onto a sensor array 112. The band-passes of filters 96 and 106, and the transmission levels of filters 100 and 110, are typically electronically selectable by controller 70. Using connection 72, controller 70 is able to receive the images acquired by sensors 102 and 112, to tune band-pass filters 96 and 106, and to set a transmission level for neutral density filters 100 and 110.

Figure 3:
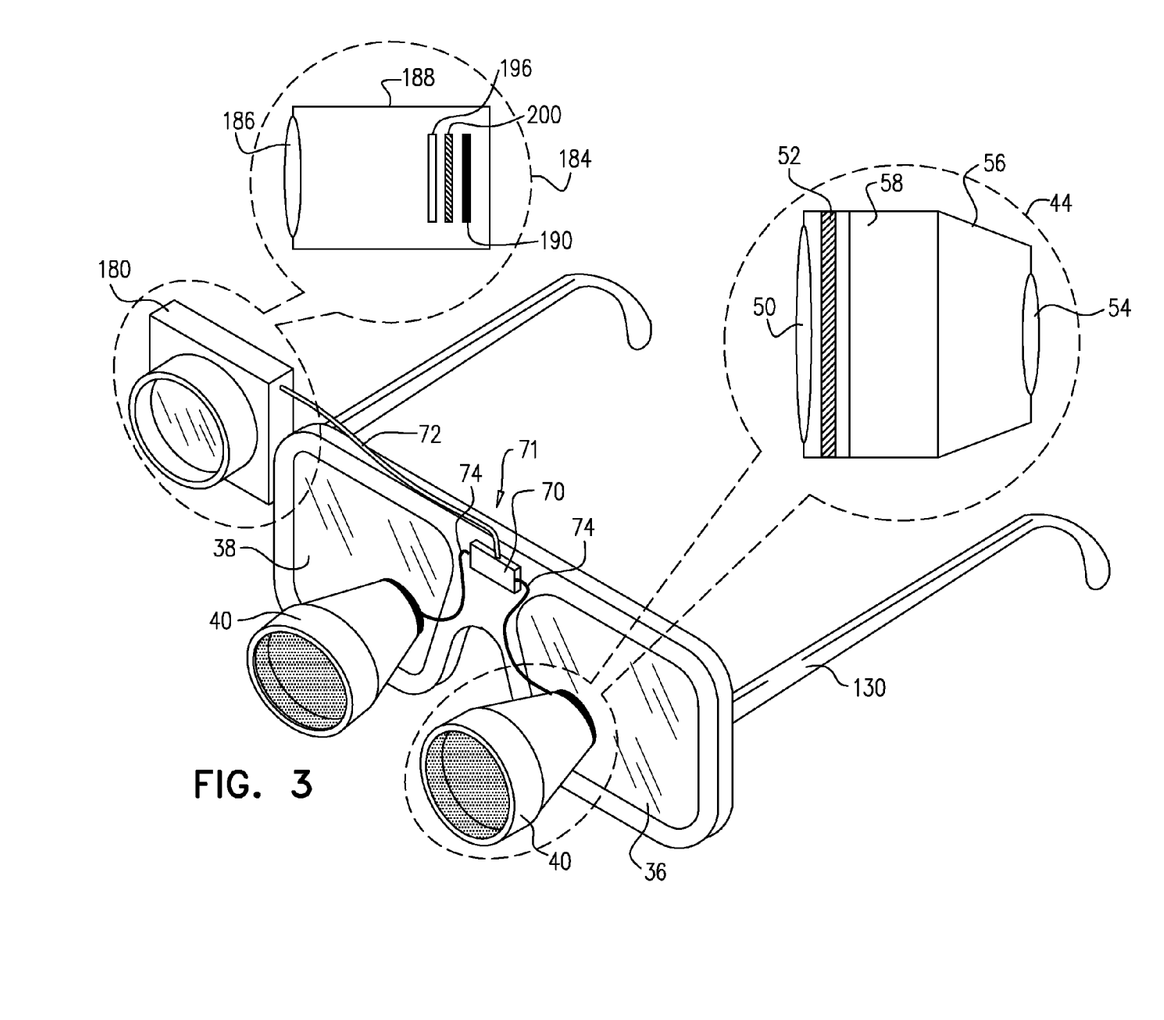
FIG. 3 is a schematic drawing of a pair of spectacles, according to an alternative embodiment of the present invention.

FIG. 3 is a schematic drawing of a pair of spectacles 130, according to an alternative embodiment of the present invention. Pair of spectacles 130 are also referred to herein as spectacles 130. Apart from the differences described below, the operation of spectacles 130 is generally similar to that of spectacles 30, and elements indicated by the same reference numerals in both spectacles 30 and 130 are generally similar in construction and in operation.

Spectacles 130 comprise a reference sensor 180, the structure of which is illustrated in an inset 184. Reference sensor 180 comprises an objective lens 186 mounted in a housing 188, but in contrast to the reference sensor of spectacles 30, the objective lens of sensor 180 is not followed by a beamsplitter. Rather, in reference sensor 180 the radiation from objective lens 186 is focused via a single path onto a sensor array 190. A tunable band-pass filter 196 and a variable neutral density filter 200 are in the single path, between lens 186 and array 190. Filters 196 and 200 are typically electronically adjustable. As for reference sensor 80, controller 70 is able to receive the image acquired by array 190, and to tune filter 196 and set filter 200 via connection 72.

In a further alternative embodiment of spectacles 130, variable neutral density filter 200 is not present in sensor 180. In this case the radiation from objective lens 186 is focused via the single path, which only includes tunable band-pass filter 196, onto sensor array 190.

The operation of spectacles 30 or 130 is described below with respect to FIG. 7.

Figure 4:
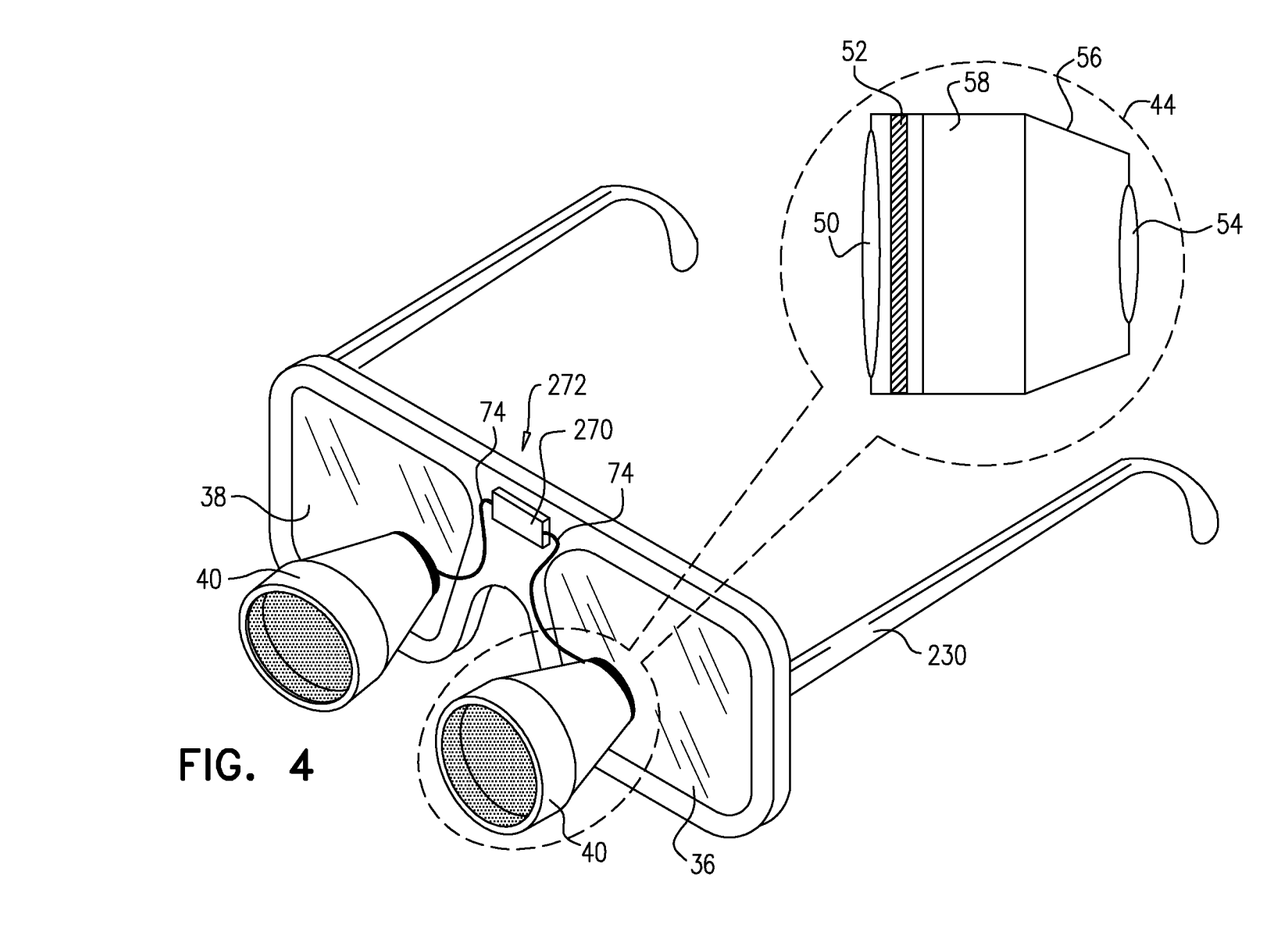
FIG. 4 is a schematic drawing of a pair of spectacles, according to a further alternative embodiment of the present invention.

FIG. 4 is a schematic drawing of a pair of spectacles 230, according to a yet further alternative embodiment of the present invention. Apart from the differences described below, the operation of spectacles 230 is generally similar to that of spectacles 130 and 30, and elements indicated by the same reference numerals in spectacles 30, 130, and 230 are generally similar in construction and in operation.

In spectacles 230 controller 70 is replaced by an autonomous controller 270 which is able to act independently, without the feedback used by controller 70, in controlling the filters of loupes 40. Thus, in spectacles 230 no reference sensor, such as sensors 80 and 180 described above, is present in spectacles 230, and there is no connection 72. In order to operate independently, pre-set data for its operation is stored in a memory 272 of the controller. The generation of the pre-set data, and the process by which controller 270 uses the data, is explained below.

Figure 5:
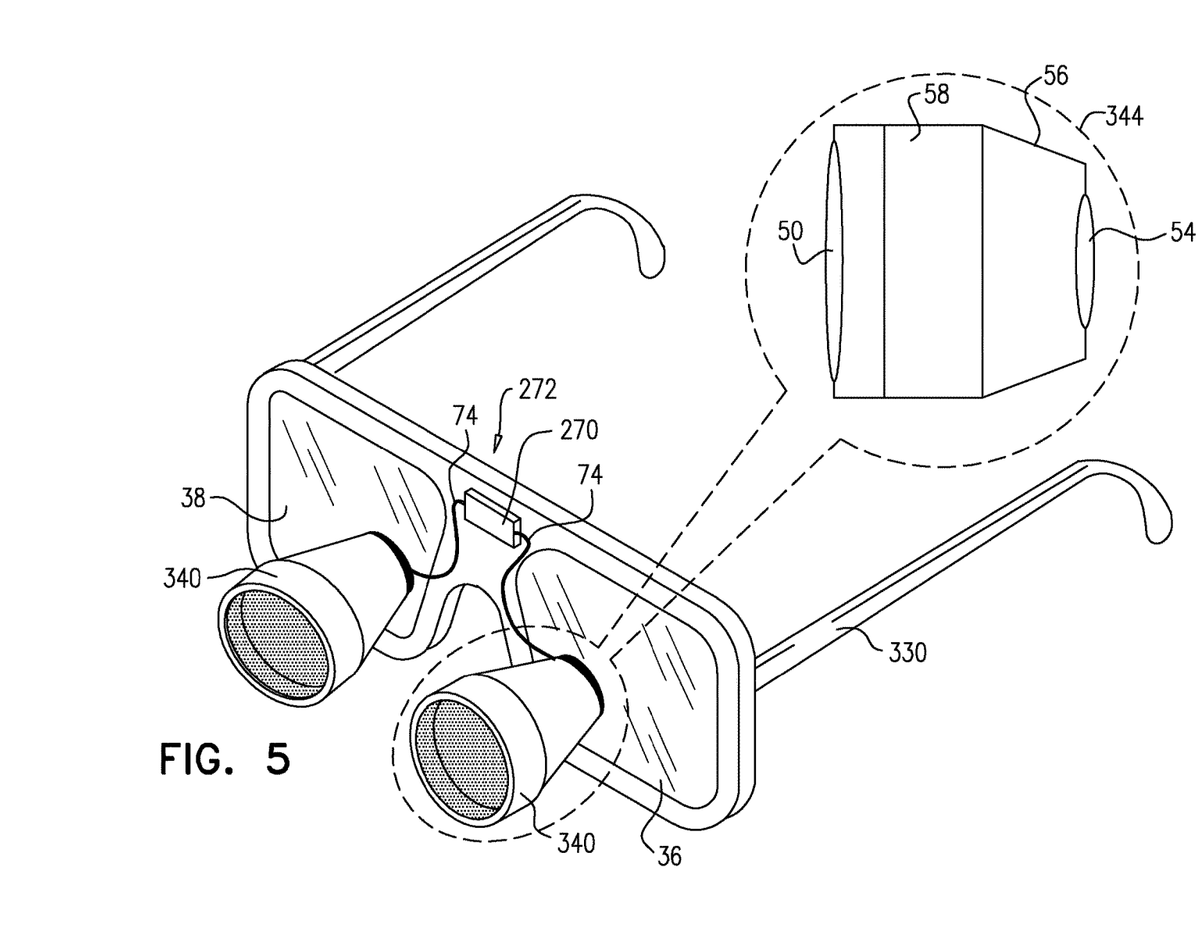
FIG. 5 is a schematic drawing of a pair of spectacles, according to a yet further embodiment of the present invention.

FIG. 5 is a schematic drawing of a pair of spectacles 330, according to a disclosed embodiment of the present invention. Apart from the differences described below, the operation of spectacles 330 is generally similar to that of spectacles 230, and elements indicated by the same reference numerals in spectacles 330 and 230 are generally similar in construction and in operation.

In spectacles 330, loupes 340 replace loupes 40. In loupes 340, the structure of which is illustrated in an inset 344, there is no neutral density filter, such as neutral density filter 52 of loupe 40. Because of the absence of a neutral density filter in loupe 340, transmission of light through the loupe is substantially only limited by tunable filter 58.

The descriptions of the spectacles above have typically assumed that the tunable wavelength filters are configured so that their narrow-band pass wavelengths are electronically selectable, and that transmission levels of the neutral density filters are also electronically selectable. Embodiments of the present invention are not limited to such electronically selectable filters, however, and include filters which are mechanically selectable. An example of spectacles using mechanically selectable filters is provided in the following description with respect to FIG. 6.

Figure 6:
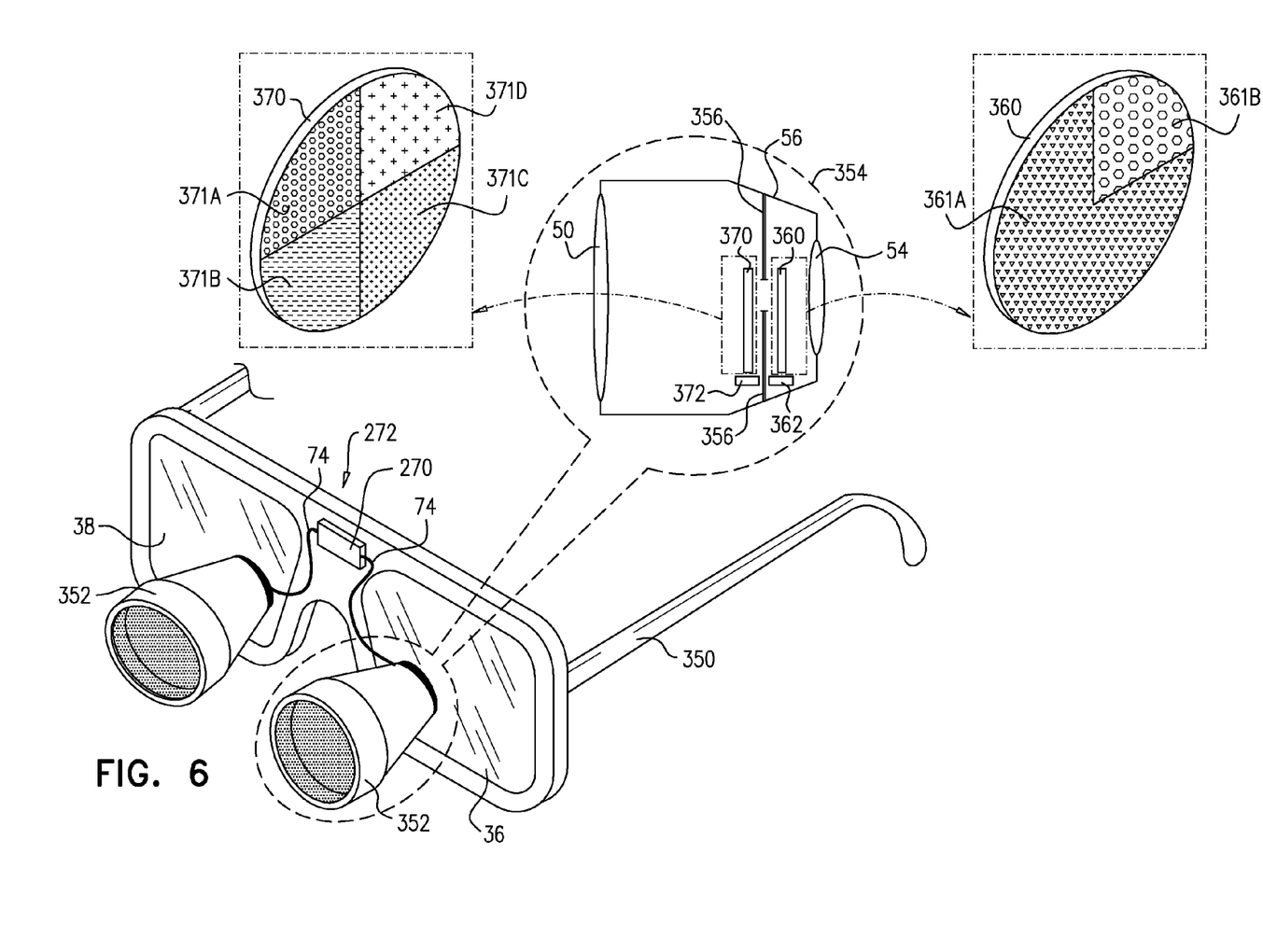
FIG. 6 is a schematic drawing of a pair of spectacles, according to a disclosed embodiment of the present invention.

FIG. 6 is a schematic drawing of a pair of spectacles 350, according to a disclosed embodiment of the present invention. Apart from the differences described below, the operation of spectacles 350 is generally similar to that of spectacles 230 (FIG. 4), and elements indicated by the same reference numerals in spectacles 350 and 230 are generally similar in construction and in operation.

In spectacles 350, loupes 352 replace loupes 40. In each loupe 352, as shown in an inset 354, a neutral density filter set 370 replaces neutral density filter 52 of loupe 40. In contrast to electronically tunable filter 52, neutral density filter set 370 comprises a set of neutral density films which are mechanically selectable. Thus, by way of example, filter set 370 comprises four neutral density films 371A, 371B, 371C, 371D having different transmission levels. The films may be mounted as a wheel, which is driven by a motor 372, typically a stepper motor, operated by controller 270. By way of example, loupe 352 is assumed to comprise optics 356, such as an iris, which provide a defined path for the light transmitted to the eye of professional 32. Thus controller 270, using motor 372, is able to mechanically select one of the films of the filter set so that it is in the defined path.

Also in each loupe 352 a narrow-band filter set 360 replaces filter 58 of loupe 40. In contrast to electronically tunable filter 58, narrow-band filter set 360 typically comprises a set of narrow pass-band films which are mechanically selectable. Thus, by way of example, filter set 360 comprises two narrow pass-band films 361A, 361B, transmitting different narrow pass-band sets of wavelengths. The films may be configured as a wheel, which is driven by a motor 362, typically similar to motor 372, operated by controller 270. Controller 270 is able to use motor 370 to mechanically position a selected one of the narrow passband films of set 360 so that it is in the defined path referred to above.

The operation of spectacles 230, 330, and 350, including in the case of spectacles 350 the selection and sizing of films 371A, 371B, 371C, 371D and films 361A, 361B, is described below with reference to FIG. 8.

Figure 7:
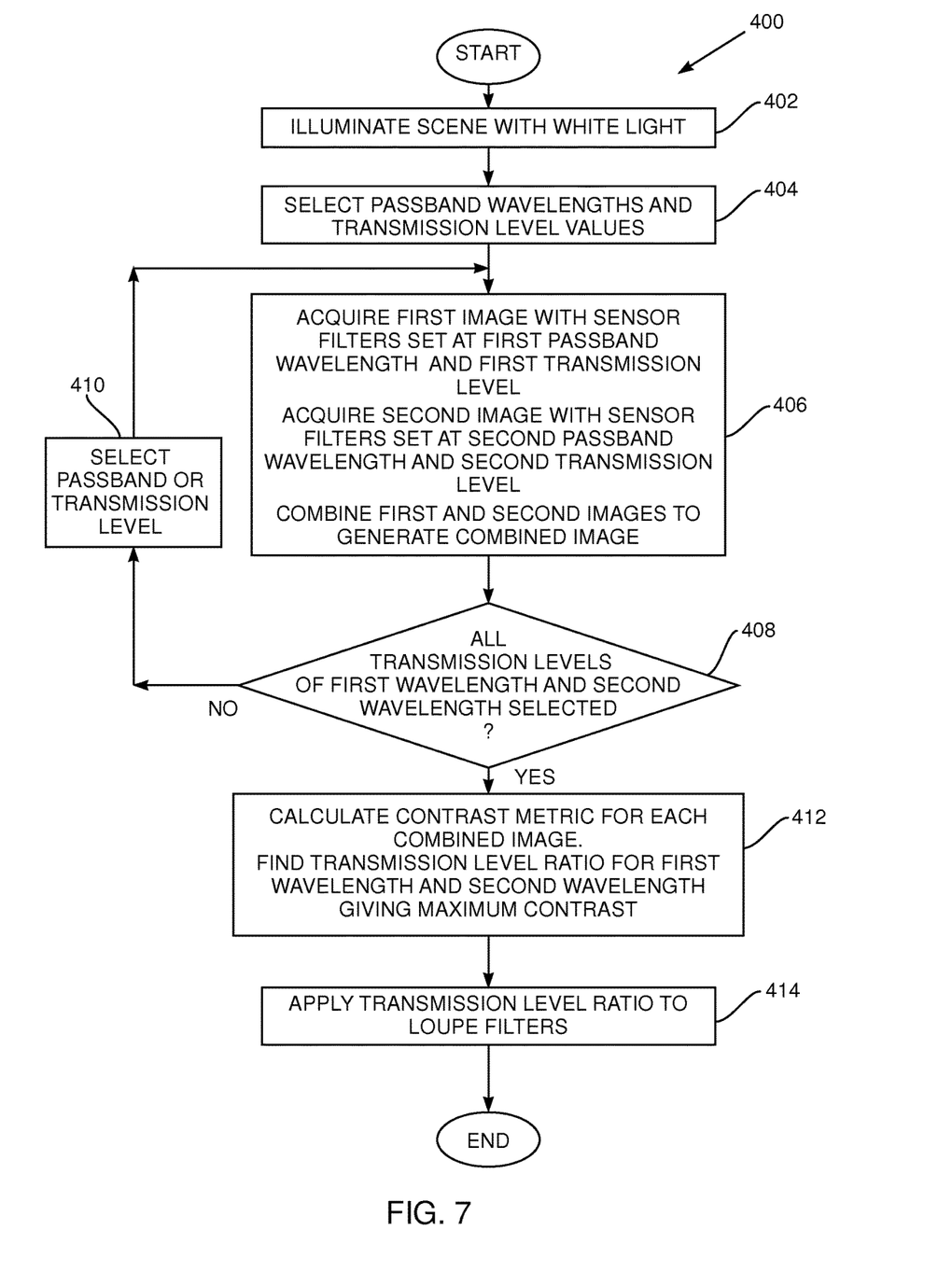
FIG. 7 is a flowchart describing steps to operate the system of FIG. 1, according to an embodiment of the present invention.

FIG. 7 is a flowchart 400 describing steps used by professional 32 to operate system 20 with spectacles 30 or spectacles 130, according to an embodiment of the present invention. In an initial step 402, the scene to be viewed by the professional is prepared, and the scene is illuminated with broadband visible light, typically substantially white light.

The following steps 404-410 describe operations involving reference sensor 80.

In a system setup step 404, for spectacles 30 the wavelengths of different narrow pass-bands to be generated by tunable narrow-band filters 96 and 106 in operating system 20 are selected. For spectacles 130 the wavelengths of different narrow pass-bands to be generated by tunable narrow-band filter 196 are selected. The selection may be made manually by professional 32, typically by prior observation of images illuminated by two or more of the passbands. For example, the professional may select four narrow pass-bands, respectively centered on 650 nm, 600 nm, 550 nm, and 450 nm, and with widths of approximately 20 nm, and store these values in memory 71 of controller 70. Alternatively, center values and ranges of the different pass-bands to be used, such as those provided above, may be pre-stored in the controller memory. In either case, controller 70 determines a pass-band to be used by accessing its memory. In the system setup step at least two different narrow pass-bands may be selected, and embodiments of the present invention typically use three or more different narrow pass-bands.

Also in step 404, the transmission levels to be applied by neutral density filters 100 and 110 are selected. As for the wavelength selection for narrow-band filters, the selection may be made manually by professional 32, or the different transmission levels may be pre-stored in the controller memory. At least two different transmission levels, and typically three or more levels, may be used. For example, transmission levels may be set at 25%, 50%, and 100% transmission. Since, as is described below, controller 70 uses a ratio of transmission levels, in implementing the flowchart one of the different transmission levels may typically be set at 100%.

It will be understood that values for the different center wavelengths and ranges of the tunable pass-band filters, and for the different transmission levels for the neutral density filters, may be different from those given above. Such different values may be determined without undue experimentation, typically by calibration using pre-set viewing scenes, by those having ordinary skill in the art.

For simplicity, the remaining steps of the flowchart assume that only two different sets of narrow-band wavelengths have been selected in step 404.

For spectacles 30, in an image acquisition step 406, controller 70 chooses a pass-band for pass-band filter 96, a different pass-band for pass-band filter 106, and the controller applies signals to the filters so that the respective pass-bands are activated simultaneously. The controller also chooses a transmission level for neutral density filters 100 and 110 and applies signals to the neutral density filters so that the respective transmission levels are activated simultaneously with the pass-bands of filters 96 and 106. Arrays 102 and 112 acquire images focused on the arrays during the activation time of the pass-band and neutral density filters. The controller then retrieves the acquired images and combines the images, typically by adding RGB (red, green, blue) values of each pixel in the image from array 102 to the RGB values of the corresponding pixel in the image from array 112. The controller stores the combined image for later analysis.

For spectacles 130, in image acquisition step 406, controller 70 chooses a first pair of a pass-band and a transmission level, and a second pair of a pass-band and a transmission level. The pass-bands in the two pairs are selected to be different. In a first time period, the controller applies signals to filter 196 and filter 200 to activate the first pair of values. During the first time period array 190 acquires a first image, and the controller retrieves and stores the first image. In a second time period, the controller applies signals to filter 196 and filter 200 to activate the second pair of values, array 190 acquires a second image, and the controller retrieves and stores the second image. The controller combines the images, typically as described above. Because the images are acquired sequentially, the controller may need to register the two images, by any convenient method known in the art, before combining them. As for spectacles 30, for spectacles 130 the controller stores the combined image for later analysis.

In a decision step 408, the controller checks to see that images have been acquired for all possible permutations of pass-band wavelengths and transmission levels. If some permutation has not been used, then in a change step 410 the controller selects a pass-band and/or transmission level that has not been set in step 404, and returns to step 406. Typically, in step 406 one of the transmission levels is set at 100%, while the other transmission level is varied.

In an analysis step 412, the controller generates an overall contrast metric for each combined image stored in step 406. The controller may use any convenient method known in the art for generating the contrast metric. For example, the controller may identify edges in the image, and use the changes in RGB values across the edges to calculate the contrast metric. Other methods for calculating a contrast metric for an image will be apparent to those having ordinary skill in the art, and all such methods are assumed to be comprised within the scope of the present invention.

The overall contrast metric is typically calculated without reference to different types of elements present in the scene being analyzed. However, in some embodiments the contrast metric is calculated for a type of element within the scene, such as blood vessels or tumors, with respect to surrounding elements. The type of element is a sub-element of the scene being analyzed, and the contrast metric in this case is referred to as a sub-element contrast metric. The calculation of the values of sub-element contrast metrics may typically be implemented by the controller applying weighting factors for the desired sub-elements, such as identified blood vessels, in the image.

For simplicity, in the remainder of the disclosure, except where otherwise indicated, the calculated contrast metric is assumed to be an overall contrast metric, and those having ordinary skill in the art will be able to adapt the description for the case of sub-element contrast metrics.

From the generated contrast metrics the controller determines a first pass-band wavelength and its associated transmission level, and a second pass-band wavelength and its associated transmission level, which together generate a combined image having a maximum value of the contrast metric. The controller calculates a transmission level ratio from the associated transmission levels.

In a loupe application step 414, the controller uses the values from analysis step 412 to tune sequentially wavelength filter 58 to the first and second pass-band wavelengths found in step 412. In synchronization with the sequential tuning for the wavelengths, the controller sequentially tunes filter 52 to respective transmission values for each wavelength, as determined in step 412, according to the transmission level ratio determined therein. The rate of sequential toggling of the wavelengths and associated transmission levels, and the duration in each toggled state, are selected so that the image viewed by the professional, because of the property of persistence of vision, is a steady image without visible flicker. The steady image has the maximum value of the contrast metric determined in step 412.

The description of steps 406-414 has assumed, for simplicity, that only two pass-bands are selected in step 404, so that controller 70 finds transmission levels for the single pair of pass-bands selected. Those having ordinary skill in the art will be able to adapt the description, mutatis mutandis, for the cases of more than two pass-bands being selected in step 304. For example, if four pass-bands are selected, then controller 70 may analyze the cases of the six different pairs of pass-bands, the four different triples of pass-bands, and the single case of all four pass-bands being used. For each of the cases, controller 70 finds a transmission level ratio giving maximum contrast in the combined image. It will be understood that, in spectacles 30, to measure up to four pass-bands simultaneously, two extra beam splitters, and two extra sets of tunable neutral density filters and tunable wavelength filters are incorporated into sensor 80.

Spectacles 30 have reference sensor 80, and spectacles 130 have reference sensor 180, the reference sensors enabling the controller of the spectacles to determine pass-bands and transmission levels at which loupes 40 operate. By acquiring an image of section 28, which is a specific scene being viewed by the loupes, the reference sensors enable controller 70 to determine specific pass-bands and transmission levels for the specific scene being viewed. Furthermore, by having a reference sensor in the spectacles, professional 32 may use the spectacles to maximize the contrast of substantially any specific scene.

In contrast to spectacles 30 and 130, spectacles 230 and 330 do not have a reference sensor. As is explained below in the flowchart describing operation of spectacles 230 and 330 (FIG. 7), controller 270 of the spectacles operates loupes 40 with pre-determined pass-bands and pre-determined transmission levels.

Figure 8:
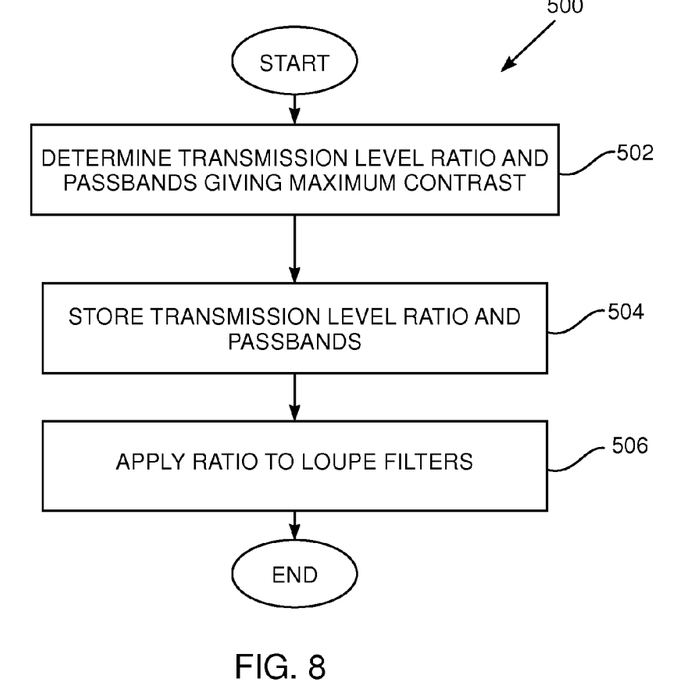
FIG. 8 is a flowchart describing steps to operate the system of FIG. 1, according to an alternative embodiment of the present invention.
Figure 9:
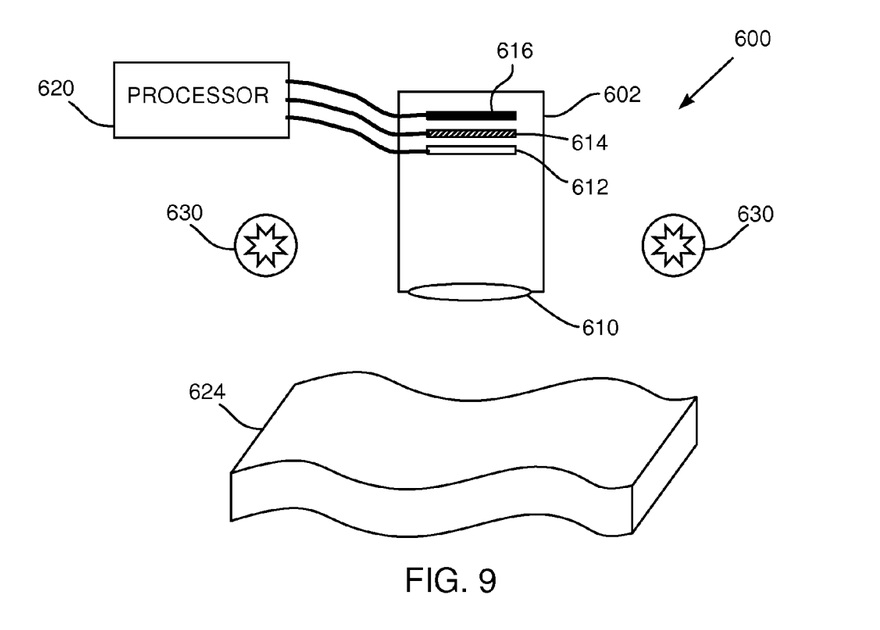
FIG. 9 is a schematic illustration of an arrangement used in performing the steps of the flowchart of FIG. 8, according to an embodiment of the present invention.

FIG. 8 is a flowchart 500 describing steps used by professional 32 to operate system 20 with spectacles 230, spectacles 330, or spectacles 350, according to an embodiment of the present invention. FIG. 9 is a schematic illustration of an arrangement 600 used in performing steps of flowchart 500, according to an embodiment of the present invention. Arrangement 600 comprises a sensing system 602, which is generally similar in operation to sensor 180, and which comprises similar elements. Thus system 602 comprises an objective lens 610, a tunable pass-band filter 612, a variable neutral density filter 614, and an array 616, which are respectively similar to lens 186, pass-band filter 196, neutral density filter 200, and array 190. A processor 620 operates the elements of system 602. A material 624, selected to have visual characteristics similar to section 28, is configured to be illuminated with broadband, substantially, white light, by lights 630. The material is fixed relative to sensing system 602.

In an initial step 502, material 624 is illuminated by lights 630, and system 602 is adjusted so that array 616 is able to acquire focused images of the material. Processor 620 varies the transmission level of filter 614, and the pass-band of filter 612. For each different transmission level and pass-band, the processor stores a respective image acquired by array 616. The processor then analyzes the stored images to find which combination of images, having two or more different pass-bands and an associated transmission level ratio, gives a maximum value of the contrast metric described above.

In a storage step 504, the pass-bands and transmission level ratio giving the maximum value of the contrast metric are stored in memory 272. Alternatively or additionally, the pass-bands and ratios may be stored in another memory used by system 20.

In an operational step 506, for spectacles 230, controller 270 accesses memory 272 and applies, for the pass-bands stored in the memory, the respective transmission level ratio. The controller applies each pass-band by activating filter 58, and by simultaneously activating neutral density filter 52 with the corresponding transmission level for the pass-band. Each pair of pass-band wavelength and corresponding transmission level are applied consecutively, at a rate sufficient so that the image observed by the professional does not flicker.

For spectacles 330, in operational step 506, controller 270 accesses memory 272 to determine pass-bands and the transmission level ratio applicable to the pass-bands. The controller implements the transmission level ratio by setting a duty cycle of the pass-bands for filter 58 to correspond to the ratio. For example, if the transmission level ratio for a blue pass-band and a green pass-band is 2:1, then filter 58 may be activated for the blue pass-band for 50 ms, and for the green pass-band for 25 ms. The controller typically switches sequentially between the two pass-bands.

For spectacles 350, in operational step 506, the transmission ratio values and the pass-band values of step 504 are used to construct neutral density filter set 370 and narrow-band filter set 360. During operation of loupes 352 controller 270 uses motors 356 and 352 to select the appropriate neutral density filter and the appropriate narrow pass-band filter from the constructed sets.

In some embodiments of spectacles 350 there is no neutral density filter set 370. Such embodiments correspond to spectacles 330 (FIG. 5), which do not have a neutral density filter. In embodiments of spectacles 350 without a neutral density filter set 370, controller 270 implements the transmission level ratio in a similar way to the setting of the duty cycle in spectacles 330. The setting of an effective duty cycle in spectacles 350 is by configuring motor 362 to vary the rate of rotation of filter set 360, and/or is by configuring filter set 360 to have differently sized narrow pass-band films. For example, if the desired transmission ratio between a narrow blue pass-band and a narrow green pass-band is 3:1, then film 361A may be selected to transmit the blue pass-band, film 361B may be selected to transmit the green pass-band, and the two films may be equally sized in set 360 as semicircles. To achieve the desired transmission ratio, motor 370 rotates film 361B three times faster than film 361B.

Alternatively, for any given transmission ratio, films 361A and 361B may be configured as correspondingly sized sectors of a circle. Thus for the transmission ratio 3:1 referred to above, film 361A may be configured as a sector subtending 270° at its center, and film 361B may be configured as a sector subtending 90° at its center, as is illustrated in FIG. 6. For such a configuration motor 370 may rotate filter set 360 at a constant rate to achieve the desired transmission ratio.

Returning to FIGS. 3 and 4, reference sensors 80 and 180 are described as using neutral density filters 100, 110, and 200 to vary the transmission levels for different pass-bands. In alternative embodiments of the present invention, there are no neutral density filters in the reference sensors, and the different transmission levels are simulated by varying the image acquisition times of arrays 102, 112, and 190. For example, in the case of reference sensor 180, a transmission level of 100% may be simulated by setting an acquisition time of 10 ms, and a transmission level of 50% may be simulated by setting the acquisition time to be 5 ms.

Returning to FIG. 9, in an alternative embodiment of sensing system 602, variable neutral density filter 614 is not present, and processor 620 may simulate transmission levels in substantially the same way as described above for reference sensor 180, by varying image acquisition times of array 616. Furthermore, it will be appreciated that methods other than those described above for system 602, for determining appropriate pass-bands and a transmission level ratio for the pass-bands, so as to obtain a combined image having a maximum contrast, will be apparent to those having ordinary skill in the art. All such methods are assumed to be included within the scope of the present invention.

In embodiments described above, filters retained by loupe housing 56 have been assumed to be retained within the housing. It will be appreciated that this is not a necessary condition for the filters, so that, for example, the filters may be configured to be retained outside the loupe housing, in which case they may be switched into and out of registration with the loupe optics, typically by a manual adjustment of the spectacle wearer.

It will thus be appreciated that the embodiments described above are cited by way of example, and that the present invention is not limited to what has been particularly shown and described hereinabove. Thus, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus, comprising:
    a housing, configured to be mounted in proximity to a human eye;
    optics, retained by the housing and configured to focus optical radiation from a scene to an image viewable by the human eye;
    a tunable wavelength filter, retained by the housing and configured to sequentially toggle between filtering the optical radiation from the scene by a first wavelength and by a second wavelength different from the first wavelength;
    a neutral density filter retained by the housing and configured to apply a first transmission level to the optical radiation filtered by the first wavelength and to apply a second transmission level to the optical radiation filtered by the second wavelength; and
    a processor configured to generate respective contrast metrics of the image for multiple different pairs of wavelengths and transmission levels, and responsively to the contrast metrics, to select the first wavelength and first transmission level and the second wavelength and second transmission level so as to maximize a contrast of the image viewable by the human eye.

2. The apparatus according to claim 1, wherein the first wavelength comprises a first narrow pass-band set of wavelengths and wherein the second wavelength comprises a second narrow pass-band set of wavelengths.

3. The apparatus according to claim 1, and comprising a reference sensor configured to acquire a reference image of the scene, and to determine the first wavelength and the second wavelength in response to a characteristic of the reference image.

4. The apparatus according to claim 3, wherein the characteristic comprises a contrast metric measuring contrast within the scene, and wherein the first wavelength and the second wavelength are determined in response to the contrast metric being a maximum.

5. The apparatus according to claim 4, wherein the contrast metric comprises a sub-element metric measuring contrast of a sub-element within the scene, and wherein the first wavelength and the second wavelength are determined in response to the sub-element metric being a maximum.

6. The apparatus according to claim 1, wherein the processor activates the tunable wavelength filter to sequentially filter at the first wavelength and the second wavelength according to a duty cycle determined in response to the first transmission level and the second transmission level.

7. The apparatus according to claim 1, wherein the scene is illuminated by broadband optical radiation, and wherein the first wavelength comprises a first pass-band wavelength narrower than the broadband optical radiation and the second wavelength comprises a second pass-band wavelength narrower than the broadband optical radiation.

8. The apparatus according to claim 1, wherein the tunable wavelength filter comprises an electronically selectable filter wherein the first wavelength and the second wavelength are electronically selectable.

9. The apparatus according to claim 1, wherein the tunable wavelength filter comprises a mechanically selectable filter wherein the first wavelength and the second wavelength are mechanically selectable.

10. A method, comprising:
    mounting in proximity to a human eye a housing retaining optics that are configured to focus optical radiation from a scene to an image viewable by the human eye;
    toggling a tunable wavelength filter that is retained in the housing to sequentially filter the optical radiation from the scene by a first wavelength and by a second wavelength different from the first wavelength;

operating a neutral density filter that is retained by the housing to apply a first transmission level to the optical radiation filtered by the first wavelength and to apply a second transmission level to the optical radiation filtered by the second wavelength;

generating respective contrast metrics of the image for multiple different pairs of wavelengths and transmission levels; and responsively to the contrast metrics, selecting the first wavelength and first transmission level and the second wavelength and second transmission level so as to maximize a contrast of the image viewable by the human eye.

11. The method according to claim 10, wherein the first wavelength comprises a first narrow pass-band set of wavelengths and wherein the second wavelength comprises a second narrow pass-band set of wavelengths.

12. The method according to claim 10, and comprising acquiring a reference image of the scene, and determining the first wavelength and the second wavelength in response to a characteristic of the reference image.

13. The method according to claim 12, wherein the characteristic comprises a contrast metric measuring contrast within the scene, and wherein the first wavelength and the second wavelength are determined in response to the contrast metric being a maximum.

14. The method according to claim 13, wherein the contrast metric comprises a sub-element metric measuring contrast of a sub-element within the scene, and wherein the first wavelength and the second wavelength are determined in response to the sub-element metric being a maximum.

15. The method according to claim 10, and comprising activating the tunable wavelength filter to sequentially filter at the first wavelength and the second wavelength according to a duty cycle determined in response to the first transmission level and the second transmission level.

16. The method according to claim 10, and comprising illuminating the scene by broadband optical radiation, and wherein the first wavelength comprises a first pass-band wavelength narrower than the broadband optical radiation and the second wavelength comprises a second pass-band wavelength narrower than the broadband optical radiation.

17. The method according to claim 10, wherein the tunable wavelength filter comprises an electronically selectable filter wherein the first wavelength and the second wavelength are electronically selectable.

18. The method according to claim 10, wherein the tunable wavelength filter comprises a mechanically selectable filter wherein the first wavelength and the second wavelength are mechanically selectable.

* * * * *